US012642598B2

(12) United States Patent
Tripathi et al.

(10) Patent No.: US 12,642,598 B2
(45) Date of Patent: Jun. 2, 2026

(54) TECHNIQUES FOR AUTOMATICALLY TRACKING SURGICAL PROCEDURES

(71) Applicant: Alcon Inc., Fribourg (CH)

(72) Inventors: Ashok Burton Tripathi, Santa Barbara, CA (US); Lu Yin, Keller, TX (US); Ramesh Sarangapani, Coppell, TX (US)

(73) Assignee: Alcon, Inc., Fribourg (CH)

( * ) Notice: Subject to any disclaimer, the term of this patent is extended or adjusted under 35 U.S.C. 154(b) by 149 days.

(21) Appl. No.: 18/495,561

(22) Filed: Oct. 26, 2023

(65) Prior Publication Data

US 2024/0138930 A1 May 2, 2024

Related U.S. Application Data

(60) Provisional application No. 63/381,259, filed on Oct. 27, 2022.

(51) Int. Cl.
*A61B 34/20* (2016.01)
*A61B 90/00* (2016.01)
(Continued)

(52) U.S. Cl.
CPC ............ *A61B 34/20* (2016.02); *A61F 2/1664* (2013.01); *G06T 7/0012* (2013.01); *G06V 10/774* (2022.01); *G06V 10/776* (2022.01); *G06V 10/945* (2022.01); *G06V 20/41* (2022.01); *G16H 10/60* (2018.01); *A61B 2034/2065* (2016.02); *A61B 2090/0805* (2016.02); *G06T 2207/30041* (2013.01); *G06V 2201/034* (2022.01)

(58) Field of Classification Search
CPC . A61B 34/20; A61B 2034/2065; A61B 90/90; A61B 2090/0805; A61F 2/1664; A61F 9/007; G16H 10/60; G06V 10/774; G06V 10/776; G06V 10/945; G06V 20/41; G06V 2201/034; G06T 7/0012; G06T 2207/30041
See application file for complete search history.

(56) References Cited

U.S. PATENT DOCUMENTS

| | | |
|---|---|---|
| 9,436,799 B2 | 9/2016 | Mccoy |
| 9,618,322 B2 | 4/2017 | Jeglorz |

(Continued)

FOREIGN PATENT DOCUMENTS

CN 101803953 A 8/2010

*Primary Examiner* — Robert A Lynch
(74) *Attorney, Agent, or Firm* — Patterson + Sheridan, LLP

(57) ABSTRACT

Certain embodiments provide a method of performing ophthalmic surgical procedures. The method includes ingesting and preparing pre-operative data and intra-operative data associated with a patient's eye for further processing. In certain embodiments, the method further includes integrating the pre-operative data and intra-operative data to generate context sensitive data for further processing. The method also includes classifying and annotating the pre-operative data, the intra-operative data, and the context sensitive data. The method also includes extracting one or more actionable inferences from the pre-operative data, the intra-operative data, context sensitive data, and the classified and annotated data. The method further includes triggering, based on the one or more actionable inferences, one or more actions on an imaging system or a surgical system.

20 Claims, 5 Drawing Sheets

304

305

(51) Int. Cl.

| | | |
|---|---|---|
| *A61F 2/16* | (2006.01) | |
| *G06T 7/00* | (2017.01) | |
| *G06V 10/774* | (2022.01) | |
| *G06V 10/776* | (2022.01) | |
| *G06V 10/94* | (2022.01) | |
| *G06V 20/40* | (2022.01) | |
| *G16H 10/60* | (2018.01) | |

(56)  References Cited

U.S. PATENT DOCUMENTS

| | | | |
|---|---|---|---|
| 2006/0129140 A1 | 6/2006 | Todd | |
| 2015/0127376 A1 | 5/2015 | Ortenzi | |
| 2018/0104100 A1 | 4/2018 | Jochinsen | |
| 2019/0110856 A1* | 4/2019 | Barral | A61B 90/37 |
| 2020/0160945 A1 | 5/2020 | Lyman | |
| 2021/0290056 A1* | 9/2021 | Karandikar | A61B 3/117 |
| 2021/0392118 A1 | 12/2021 | Sughrue | |

* cited by examiner

Figure 2:
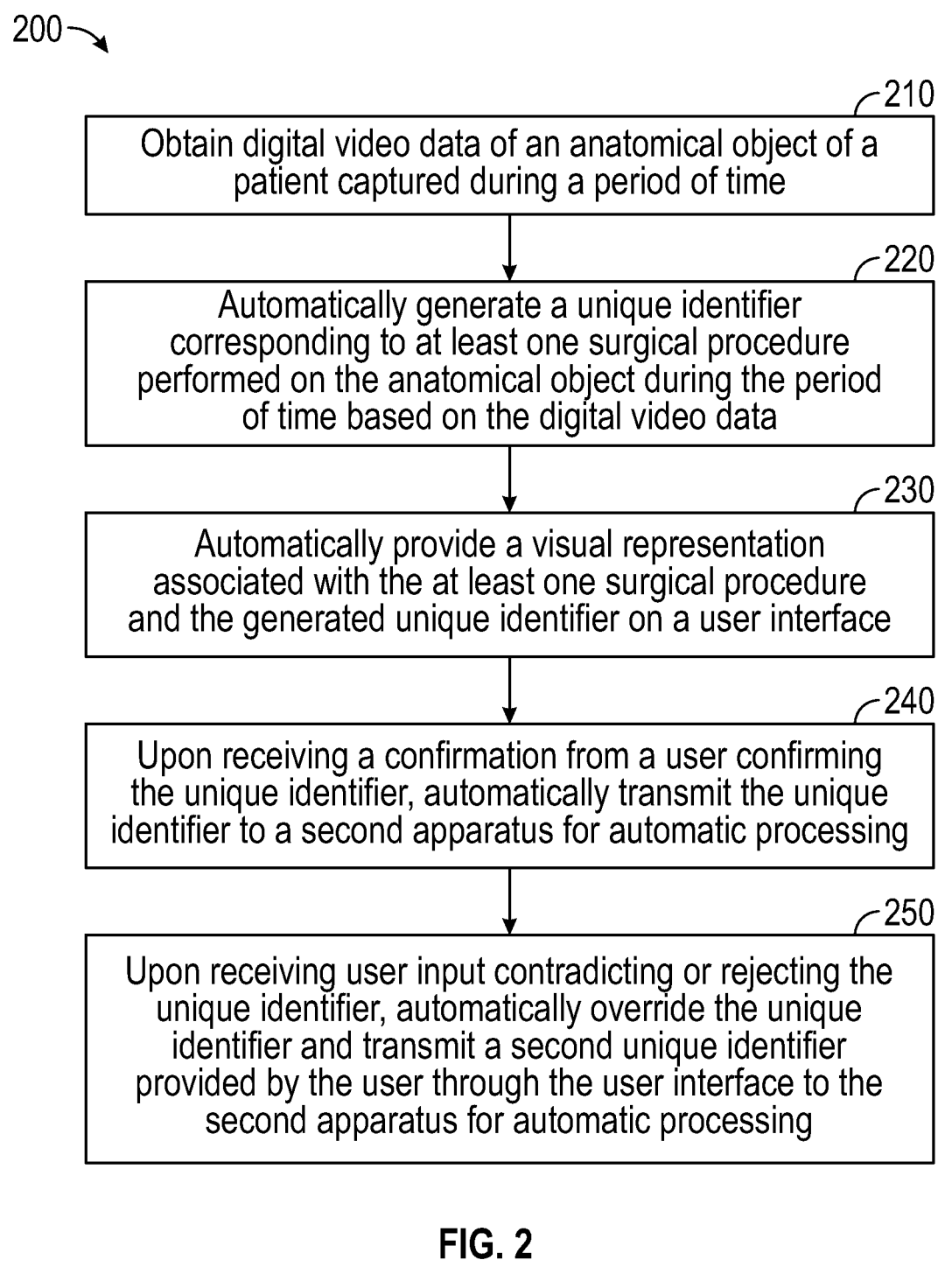

200

┌─────────────────────────────────────────────────────┐ ⌐210
│ Obtain digital video data of an anatomical object of a │
│      patient captured during a period of time          │
└─────────────────────────────────────────────────────┘

┌─────────────────────────────────────────────────────┐ ⌐220
│         Automatically generate a unique identifier      │
│    corresponding to at least one surgical procedure     │
│  performed on the anatomical object during the period   │
│         of time based on the digital video data         │
└─────────────────────────────────────────────────────┘

┌─────────────────────────────────────────────────────┐ ⌐230
│        Automatically provide a visual representation    │
│    associated with the at least one surgical procedure  │
│   and the generated unique identifier on a user interface │
└─────────────────────────────────────────────────────┘

┌─────────────────────────────────────────────────────┐ ⌐240
│   Upon receiving a confirmation from a user confirming  │
│  the unique identifier, automatically transmit the unique │
│ identifier to a second apparatus for automatic processing │
└─────────────────────────────────────────────────────┘

┌─────────────────────────────────────────────────────┐ ⌐250
│ Upon receiving user input contradicting or rejecting the │
│    unique identifier, automatically override the unique  │
│      identifier and transmit a second unique identifier  │
│   provided by the user through the user interface to the  │
│      second apparatus for automatic processing           │
└─────────────────────────────────────────────────────┘

TECHNIQUES FOR AUTOMATICALLY TRACKING SURGICAL PROCEDURES

CROSS-REFERENCE TO RELATED APPLICATIONS

This application claims the benefit of priority of U.S. Provisional patent application Ser. No. 63/381,259 titled "TECHNIQUES FOR AUTOMATICALLY TRACKING SURGICAL PROCEDURES," filed on Oct. 27, 2022, which is hereby incorporated by reference in its entirety as though fully and completely set forth herein.

BACKGROUND

A variety of diseases or conditions associated with an eye may be treated through ophthalmic surgical procedures. Examples of ophthalmic surgical procedures include vitreo-retinal surgery, cataract surgery, glaucoma surgery, laser eye surgery (LASIK), etc.

A vitreo-retinal surgery is a type of eye surgery that treats problems with the retina or the vitreous. Vitreo-retinal surgery may be performed for treating conditions such as diabetic traction retinal detachment, diabetic vitreous hemorrhage, macular hole, retinal detachment, epimacular membrane, and many other ophthalmic conditions. Cataract surgery involves emulsifying the patient's crystalline lens with an ultrasonic hand piece and aspirating it from the eye. An intraocular lens (IOL) is then implanted in the lens capsule of the eye. During vitreo-retinal, cataract, and other types of surgeries mentioned above and known to one of ordinary skill in the art, various deficiencies may negatively impact the outcome, efficiency, and effectiveness of the surgery and the surgeon's ease of performing the surgery as well as, in certain cases, cause harm to the patient's optical anatomy, etc.

BRIEF SUMMARY

One aspect of the present disclosure provides a method for automatically tracking surgical procedures performed on an anatomical object of a patient. The method includes obtaining imaging data of the anatomical object of the patient captured during a period of time, automatically generating a unique identifier corresponding to at least one surgical procedure performed on the anatomical object during the period of time based on the imaging data, automatically providing a visual representation associated with the at least one surgical procedure and the generated unique identifier on a user interface, upon receiving a confirmation from a user confirming the unique identifier, automatically transmitting the unique identifier to a second apparatus for automatic processing, and, upon receiving user input contradicting or rejecting the unique identifier, automatically overriding the unique identifier and transmitting a second unique identifier provided by the user through the user interface to the second apparatus for automatic processing.

Other aspects provide: an apparatus operable, configured, or otherwise adapted to perform the aforementioned methods as well as those described elsewhere herein; a non-transitory, computer-readable media comprising instructions that, when executed by a processor of an apparatus, cause the apparatus to perform the aforementioned methods as well as those described elsewhere herein; a computer program product embodied on a computer-readable storage medium comprising code for performing the aforementioned methods as well as those described elsewhere herein;

and an apparatus comprising means for performing the aforementioned methods as well as those described elsewhere herein. By way of example, an apparatus may comprise a processing system, a device with a processing system, or processing systems cooperating over one or more networks.

The following description and the appended figures set forth certain features for purposes of illustration.

BRIEF DESCRIPTION OF THE DRAWINGS

The appended drawings depict only examples of certain embodiments of the present disclosure and are therefore not to be considered as limiting the scope of this disclosure.

FIG. 2 illustrates example operations for use by an ophthalmic surgical system, such as the digital awareness system, in accordance with certain embodiments.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

While features of the present invention may be discussed relative to certain embodiments and figures below, all embodiments of the present invention can include one or more of the advantageous features discussed herein. In other words, while one or more embodiments may be discussed as having certain advantageous features, one or more of such features may also be used in accordance with various other embodiments discussed herein. In similar fashion, while exemplary embodiments may be discussed below as device, instrument, or method embodiments it should be understood that such exemplary embodiments can be implemented in various devices, instruments, and methods.

Digitally Aware Surgical System

Certain embodiments herein describe a digitally aware surgical system that, among other things, is configured to automatically tracking one or more surgical procedures performed on the patient, including identifying the one or more surgical procedure, capturing imaging data (e.g., photographic data and/or video data) of the one or more surgical procedures, generating one or more unique identifiers associated with the one or more surgical procedures, transmitting information to an EMR database including the photographic evidence and the one or more unique identifiers, and/or other actions described in more detail below.

The digitally aware surgical system described herein has at least four key technical capabilities including (1) the capability to analyze data in real time, (2) capability to process multi-model data (i.e., data that is generated and/or received in different formats simultaneously, such as surgical videos, numerical data, voice data, text, images, signals, etc.), (3) capability to process data received from a single source or from multiple sources simultaneously (e.g., images captured by a camera, internal sensor data, voice recording from a microphone), and (4) capability to make inferences using the received and processed data in relation to the status or stage of the surgical procedure, surgical instrumentation, status of the patient or their eye, controlling surgical equipment.

The digital awareness technology, described herein, can deliver smart functionality for surgical systems. Smart functionality for ocular surgical systems can take multiple forms in the operating room (OR), such as, image guidance based operations, patient monitoring, virtual assistant for the surgeon, and/or service automation. Incorporating the smart functionality, described by the embodiments herein, results in many improvements over existing surgical systems. The improved surgical systems described herein are capable of assisting surgeons in performing surgical tasks with higher accuracy, efficiency, and/or safety, ultimately leading to a better surgical outcome for each patient.

Figure 1:
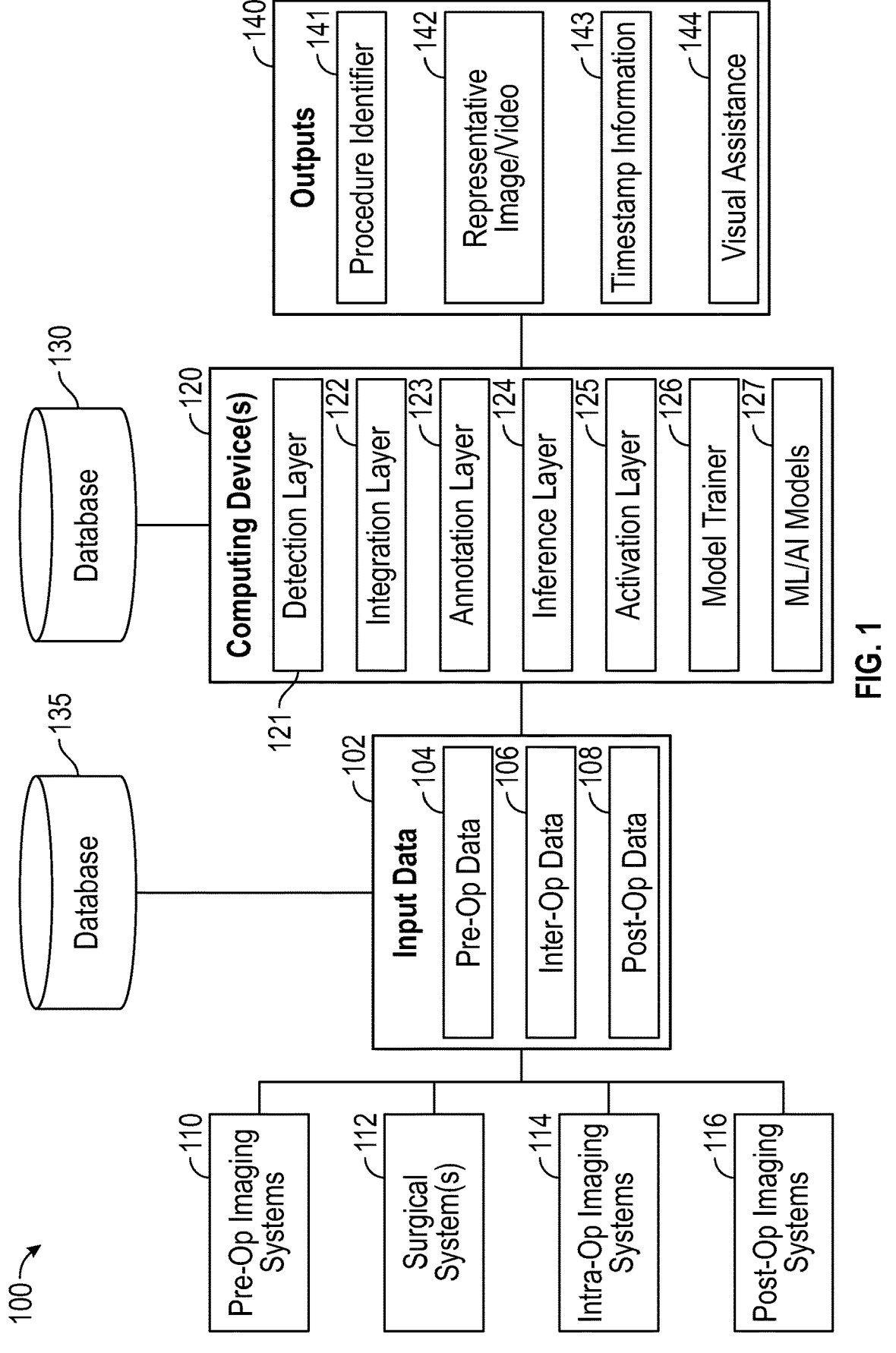
FIG. 1 illustrates an example of a digitally aware system (hereinafter "digital awareness system") configured with digital awareness technology, according to some embodiments.

FIG. 1 illustrates an example of digitally aware system 100 (hereinafter "digital awareness system") configured with digital awareness technology, according to some embodiments. As shown, digital awareness system 100 includes a variety of systems, such as one or more pre-operative (hereinafter "pre-op") imaging systems 110, one or more surgical systems 112, one or more intra-operative (hereinafter "intra-op") imaging systems 114, and post-operative (hereinafter "post-op") imaging systems 116.

Pre-op imaging systems 110, surgical systems 112, intra-op imaging systems 114, and post-op imaging system 116 may be co-located or located in various locations, including diagnostic clinics, surgical clinics, hospitals, and other locations. Whether co-located or located across various locations, systems 110, 112, 114, and 116 may each generate data that can be communicated and used as part of input data 102 over one or more networks (e.g., a local area network, a wide area network, and/or the Internet) to other systems 110, 112, 114, and 116, computing device(s) 120, and/or to databases 130 and 135.

Pre-op imaging systems 110 may refer to any number of diagnostic systems that may be used, prior to surgery, e.g., at a clinic for obtaining multi-dimensional images and/or measurements of ophthalmic anatomy such as an optical coherence tomography (OCT) system, a rotating camera (e.g., a Scheimpflug camera), a magnetic resonance imaging (MRI) system, a keratometer, an ophthalmometer, an optical biometer, a topographer, a retinal camera, a digital microscope, and/or any other type of optical measurement/imaging system. Examples of OCT systems are described in further detail in U.S. Pat. No. 9,618,322 disclosing "Process for Optical Coherence Tomography and Apparatus for Optical Coherence Tomography" and U.S. Pat. App. Pub. No. 2018/0104100 disclosing "Optical Coherence Tomography Cross View Image", both of which are hereby incorporated by reference in their entirety.

Surgical systems 112 may refer to any number of systems for performing a variety of ophthalmic surgical procedures. As an example, surgical system 112 may include consoles for performing vitreo-retinal surgeries (e.g., Constellation console manufactured by Alcon Inc., Switzerland), cataract surgeries (e.g., Centurion console manufactured by Alcon Inc., Switzerland), and many other systems used for performing a variety of ophthalmic surgeries, as known to one of ordinary skill in the art. Note that, herein, the term "system" is also inclusive of the terms console and device.

Intra-op imaging systems 114 may include any systems that may obtain imaging data (e.g., video data, image frames, metadata, etc.) as well as measurements associated with a patient's eye during a surgical procedure. An example of an intra-operative imaging system 114 used for cataract surgery is the Ora™ with Verifeye™ (Alcon Inc., Switzerland), which is used to provide intra-operative measurements of the eye, including one or more of the curvature of the cornea, axial length of the eye, white-to-white diameter of the cornea, etc. Other types of intra-op systems used for generating and providing intra-op data may include digital microscopes comprising one or more digital cameras, such as three-dimensional stereoscopic digital microscopes (e.g., NGENUITY® 3D Visualization System (Alcon Inc., Switzerland). A variety of other intra-op imaging systems may also be used, as known to one of ordinary skill in the art.

Post-op imaging systems 116 may refer to any number diagnostic systems that may be used, post-surgery, at a clinic for obtaining multi-dimensional images and/or measurements of ophthalmic anatomy. Post-op imaging systems 116 may be the same as pre-op imaging systems 110, described above.

Input data 102 includes pre-op data 104, intra-op data 106, and post-op data 108. Pre-op data 104 may include information about the patient, including data that may be received from database 135 (e.g., a database, such as an electronic medical record (EMR) database for storing patient history information) and data that is generated and provided by pre-op imaging systems 110 about the patient's eye. For example, pre-op data 104 may include patient history information, including one or more relevant physiological measurements for the patient that are not directly related to the eye, such as one or more of age, height, weight, body mass index, genetic makeup, race, ethnicity, sex, blood pressure, other demographic and health related information, and/or the like. In some examples, the patient history may further include one or more relevant risk factors including smoking history, diabetes, heart disease, other underlying conditions, prior surgeries, and/or the like and/or a family history for one or more of these risk factors. In some embodiments, the patient history information may include information related to a medication history of the patient, such as a list of medications currently being taken by the patient, a list of medications previously taken by the patient, a list of medications that the patient is allergic to, and the like.

Data that is generated and provided by pre-op imaging systems 110 about the patient's eye may include one or more pre-op measurements and images as well as any measurements or other types of information extracted from the one or more pre-op images. As an example, pre-op images may include images of one or more optical components of the eye (e.g., retina, vitreous, crystalline lens, cornea, etc.). Pre-op measurements may include the patient's axial length of the eye, corneal curvature, anterior chamber depth, white-to-white diameter of the cornea, lens thickness, effective lens position, as well as measurements relating to retinal diseases and other conditions, as known to one of ordinary skill in the art.

Intra-op data 106 may include any information obtained or generated during or as a result of the patient's surgical procedure. For example, intra-op data 106 may include data inputted into (e.g., by a user), or generated and provided (e.g., automatically) by surgical systems 112 as well as intra-op imaging systems 114, which may be present in an operating room during the patient's surgical procedure. In particular, such intra-op imaging data may include one or more intra-operative images and/or measurements, including images and/or measurements of the eye obtained as the procedure is being performed.

Examples of intra-op data 106 includes imaging data, such as surgical videos (e.g., video data) and images (e.g., image frames), captured by a digital microscope/digital camera. In some embodiments, the imaging data may include video/image data of one or more surgical procedures performed on the patient's eye. The intra-op data 106 may also include images captured by a surgical microscope, surgical system data that includes system parameters, active settings, and UI/UX/control status set by a surgeon or the staff. The intra-op data 106 may also include other data modality pertinent to the surgeon who is interacting with the system, such as voice commands, gesture-based commands, or commands that can be received by tracking eye gaze of the surgeon, patient monitoring information (e.g., a patient eye position obtained by a system other than a surgical microscope). In some cases, the intra-op data 106 may also include certain machine settings of the surgical systems 112. For example, for a cataract surgical procedure, the machine settings may include fluidic settings, an intraocular pressure setting, a phaco energy setting, any state of any device connected to the surgical systems 112, a laser power setting, a laser intensity setting, a total laser energy applied setting, frequency of ultrasonics, power level of ultrasonics, various other settings or states of a console used for a cataract surgical procedure, and the like. In another example, for a vitreo-retinal procedure, machine settings associated with operations of a vitrectomy probe, aspiration/irrigation operations, etc. may be recorded and used as part of intra-op data 106.

In some embodiments, the voice commands may include commands by a surgeon to an intra-op imaging system 114, a surgical system 112 (e.g., console), any other system in the operating room, a nurse, or medical staff, such as requests for specific medical instruments or drugs. In some embodiments, the intra-op data 106 may include data obtained from sensors embedded in an intra-op imaging system 114 and/or a surgical system 112, for example, indicating a status or usage of certain medical instruments or systems (e.g., Alcon Centurion Phaco system, or Alcon Verion Image Guidance system) during a surgical procedure. For example, a surgical console used for cataract surgery may be configured with a sensor to indicate whether a phacoemulsification probe is being used by the surgeon. In some embodiments, the intra-op data 106 includes an inventory record associated with a patient's surgical procedure, indicating records of medical instruments or medications prepared for use during the surgical procedure. The inventory record may be complied as a result of data generated by intra-op imaging system 114 and/or a surgical system 112 throughout the surgery. In some embodiments, the intra-op data 106 includes surgical procedure specific data associated with the patient's optical components, such as the cornea, cataract, vitreoretinal components, MIGS related components (e.g., details pertinent to a cataract procedure including an incision position, IOL types, injector type, illumination settings, etc.). Additional details regarding input data 102, such as intra-op data 106, will be described below with respect to FIG. 2.

Post-op data 108 may include one or more post-op measurements and images as well as any measurements or other information extracted from the one or more post-op images. Post-op data 108 may also include patient outcome data, including a post-op satisfaction score. Patient outcome data may also be in relation to treatment efficacy and/or treatment related safety endpoints. Post-op data 108 may be particularly important for algorithm training and to continuously improve the performance of digital awareness system 100.

Computing device(s) 120 may refer to one or more co-located or non-co-located systems that execute layers of instructions shown as detection layer 121, integration layer 122, annotation layer 123, inference layer 124, activation layer 125. Computing device(s) 120 also execute a model trainer 126 as well as one or more machine learning (ML)/ artificial intelligence (AI) models 127. In certain embodiments, computing device(s) 120 may be cloud-based (e.g., private or public cloud) or located on premises ("on-prem"), or a combination thereof.

In certain embodiments, when there are multiple computing devices 120, different instructions (e.g., instruction layers 121-125, model trainer 126, and ML/AI models 127) may be executed by different computing devices 120. For example, one of the multiple computing devices 120 may be configured to execute detection layer 121 and another one of the multiple computing devices 120 may execute ML/AI models 127. In another example, one of the multiple computing devices 120 may be configured to execute detection layer 121 and another one of the multiple computing devices 120 may be configured to execute integration layer 122. In certain embodiments, one or more instruction layers 121-125, model trainer 126, and ML/AI models 127 may be executed by multiple computing devices 120 in a distributed and decentralized manner. In certain embodiments, one or more of computing devices 120 may be or include one or more of imaging systems 110, 114, and 116, and surgical systems 112 that are used to obtain ophthalmic information or perform ophthalmic surgical procedures, respectively, as described above.

During surgery, instruction layers 121-125 and ML/AI models 127 may be executed to take input data 102 for a specific patient for whom the surgery is being performed and provide certain outputs, such as outputs 140.

For example, detection layer 121 is configured to ingest input data 102 or any portion thereof and prepare the input data for further processing. For example, detection layer 121 receives various input data 102 from various sources (e.g., pre-op imaging systems 110, surgical systems 112, intra-op imaging systems 114, post-op imaging systems 116, database 135, etc.) and prepares the various input data, which may be in different formats, for ingestion by the integration layer 122. As an example, the format with which input data is received from a surgical console may be different from the format with which imaging data is received from an intra-op imaging system. Therefore, detection layer 121 may alter the format of the various input data so as to make all types of input data ingestible by the integration layer 122. For example, in some embodiments, the pre-op data 104 may only include image data whereas the intra-op data 106 may have both intra-op image data and text entries. The detection layer 121 may be configured to unify a data format, for example, by tagging the text entries to the intra-op image data and send the tagged intra-op image data to the integration layer 122. Yet another example of input data 102 is UI menu selections provided (e.g., by a user) on a UI of a surgical system 112. The UI menu selection can be converted to a procedure identifier used by the inference layer 124 below.

Integration layer 122 integrates various input data provided by detection layer 121 (e.g., intra-op data 106, pre-op data 104, etc.) to generate context sensitive information for further processing. In certain embodiments, integration layer 122 may take various forms of intra-op data 106 and integrate them together. As an example, integration layer 122 may integrate imaging data provided by an intra-operative digital microscope with other input data generated by a surgical console during the operation. In certain embodiments, integrating the various input data together may be performed by corresponding the time-stamps associated with the different streams of input data. For example, time-stamped data generated by sensors embedded in a surgical console indicative of a phaco probe being used may be integrated with time-stamped video or image data generated by a digital microscope. The time-stamps may be provided as part of the metadata associated with the various streams of input data.

In certain embodiments, integration layer 122 may integrate pre-op data 104 with intra-op data 106. For example, integration layer 122 may integrate a patient's pre-op image data with the patient's intra-op image data based on the metadata, which may indicate the patient's identity, etc. Integration layer 122 may transform the pre-op image data to a scale that matches an intra-op view so that the pre-op image data may be seamlessly overlaid onto the intra-op view.

Annotation layer 123 may be configured to use one or more of the ML/AI models 127 to classify and annotate data generated by detection layer 121 and/or integration layer 122. For example, in some embodiments, the annotation layer 123 may be configured to obtain, from the detection layer 121, the imaging data of one or more surgical procedures performed on a patient's eye. The annotation layer 123 may then be configured (e.g., trained) to then automatically label one or more objects (e.g., surgical instruments, consoles, optical components of the eye, medicine, etc.) in each of the image frames. The annotation layer 123 may be trained to label objects in image frames using an "annotation training dataset" with, for example, manually labeled images. In some embodiments, the annotation layer 123 processes a continuous flow of imaging data, and takes account of not only current or instant imaging data, but also previous imaging data.

Inference layer 124 may be configured with algorithms designed to extract one or more actionable inferences from the data that is generated by detection layer 121, integration layer 122, and/or annotation layer 123. In other words, data generated by detection layer 121, integration layer 122, and/or annotation layer 123 is used as input to inference layer 124. For example, in some embodiments, the inference layer 124 may be configured (e.g., trained) to identify a surgical procedure (e.g., by generating a respective unique identifier, such as a billing code) based on objects identified in the imaging data by the annotation layer 123 as well as any other input described above. In some embodiments, the surgical procedure may be identified in a number of ways. For example, in some embodiments, the inference layer 124 may be configured to generate a unique identifier associated with the surgical procedure, such as a billing code. In some embodiments, the inference layer 124 may be configured to generate a complexity level associated with the surgical procedure or a flag indicating that the surgical procedure is a complex case. In some embodiments, as described herein, the output of the inference layer 124 (e.g., billing code, complexity level, flag, etc.) may be generated to automatically keep track of the surgical procedures performed on a patient (e.g., to reduce a record keeping burden on a surgeon or staff) and to help reduce the chances that surgical procedures for a patient are improperly billed.

In some embodiments, some or all functions of the annotation layer 123 and inference layer 124 may be combined. For example, in some embodiments, rather than using a first one or more ML/AI models for identifying one or more objects in each image frame and, thereafter, using a second set of one or more ML/AI models for associating the respective unique identifiers with the one or more objects, the one or more ML/AI models 127 may be trained to take the output of the detection layer 121 and/or integration layer 122 and directly generate unique identifiers associated with the one or more surgical procedures performed in the imaging data. As an example, in such embodiments, a ML/AI model 127 (e.g., a deep learning model) may be trained using a training dataset, including a plurality of training data entries or records, each including a plurality of data points from input data 102 as well as a label (e.g., a respective unique identifier, such as a billing code) that identifies a surgical procedure.

Activation layer 125 may be configured with algorithms designed to trigger a set of defined downstream events based on output from inference layer 124. Example outputs of activation layer 125 is shown as outputs 140 and described in more detail below.

Model trainer 126 includes or refers to one or more AI-based learning algorithms (referred to hereinafter as "AI-based algorithms") that are configured to use training datasets stored in a database (e.g., database 130) to train ML/AI models 127. Examples of AI-based algorithms are optimization algorithms such as gradient descent, stochastic gradient descent, non-linear conjugate gradient, etc.

In certain embodiments, a trained ML/AI model 127 refers to a function, e.g., with weights and parameters, that can be used by one or more instruction layers 121-125 to make predictions and determinations based on the input data 102. A variety of ML/AI models 127 may be trained for and used by different instruction layers 121-125 for different purposes. Example ML models may include different types of neural networks, such as long short-term memory (LSTM) networks, 3D convolutional networks, deep neural networks, or many other types of neural networks or other machine learning or AI models, etc. Additional details regarding the instruction layers 121-125, model trainer 126, and ML/AI models 127 will be explained below with respect to FIG. 2.

Database 130 may refer to a database or storage server configured to store input data 102 associated with each patient as well as training datasets using by model trainer 126 to train ML/AI models 127. Training datasets may include population-based data as well as personalized data.

As shown, output 140 is categorized into a number of different outputs, including a procedure identifier 141, a representative image/video 142, timestamp information 143, and visual assistance 144. As described above, outputs 140 may be triggered by computing device(s) 120, such as annotation layer 123, inference layer 124, activation layer 125, etc. Any of the types of outputs 140 discussed above may be provided or caused to be provided by one or more software applications executing on one or more of imaging systems 110, 114, and, 116, surgical systems 112, or visualization systems (e.g., NGENUITY® 3D Visualization System).

Procedure identifier 141 refers to a unique identifier, generated at least in part based on the intra-op data 106 (e.g., imaging data), which corresponds to at the least one surgical procedure performed on the patient's eye. In some embodiments, the unique identifier may include, for example, a billing code corresponding to the surgical procedure.

Representative image/video 142 refers to a representative image frame or a representative video clip from the intra-op data 106 that demonstrates the at least one surgical procedure, or at least a certain segment thereof, performed on the eye. In some embodiments, the representative image/video 142 may be used to document a billing event associated with the at least one surgical procedure performed on the eye.

Timestamp information 143 refers to a timestamp corresponding to the representative image frame or the representative video clip included in the representative image/video 142. For example, the timestamp information 143 indicates a time at which the representative image frame or the representative video clip was generated. The timestamp information 143 may also indicate the time at which the corresponding surgical procedure, or a segment thereof, was performed.

Visual assistance 144 refers to a visual representation, associated with the at least one surgical procedure and the unique identifier corresponding to the at least one surgical procedure, which can be provided on a user interface to provide visual assistance to a user (e.g., surgeon, nurse, medical staff). In some embodiments, the user interface may allow the user to confirm or reject the unique identifier corresponding to the at least one surgical procedure. In some embodiments, the user interface may allow the user to select a second unique identifier corresponding to the at least one surgical procedure. In some embodiments, the user interface may allow the user to confirm or reject the representative image frame or the representative video clip included in the representative image/video 142. In some embodiments, if the representative image frame or the representative video clip is rejected by the user, the user interface may allow the user to select another representative image frame or another representative video clip. Additional details regarding outputs 140 will be described below with respect to FIG. 2.

Aspects Related to Automatically Tracking Surgical Procedures

Modern ophthalmic surgeries, such as cataract surgery, are associated with few complications. Although relatively rare, these complications may require a surgeon to perform one or more additional surgical procedures, which can be time consuming, complicated, and expensive. For example, during cataract surgery and IOL placement in a patient's eye, a surgeon may discover looseness in a capsular bag of the patient's eye, which potentially impacts the long term stability of the IOL. In response, the surgeon may perform an additional surgical procedure to insert a capsular tension ring (CTR) stabilizing the capsular bag. Another example of a complication that may occur during cataract surgery is associated with floppy iris syndrome in which an iris of a patient's eye will not dilate chemically, which is oftentimes linked to a medication used to treat enlarged prostate. In such cases, surgeons may perform another surgical procedure to insert iris hooks or a Malyugin ring to manually open a patient's iris that will not dilate chemically.

These complications and additional surgical procedures represent deviations from an expected surgical protocol, which take a significant amount of time to perform and add to the expense of the procedure. Due to these complications and additional surgical procedures, insurance companies may provide for additional reimbursement. To obtain the additional reimbursement, a billing code associated with the additional surgical procedures may need to be submitted to the insurance companies. In the case of cataract surgery, when no complications occur, the billing code used for compensation may be labelled under the moniker, "standard cataract." However, when complications do occur and additional reimbursement is required, the billing code for this additional reimbursement may be labelled under the moniker, "complex cataract."

In order to bill for this additional reimbursement over a "standard cataract" surgery, the surgeon (or their staff) may need to perform additional record keeping in order to provide the necessary documentation to the insurance companies to obtain compensation for the one or more additional surgical procedures performed during a "complex cataract" surgery. While the example described above relates to cataract surgery, it should be understood that deviations from standard surgical protocol associated with any type of surgery may lead to additional record keeping in order to obtain additional compensation. In many cases, however, these additional record keeping steps are time consuming, cumbersome, and prone to clerical errors.

For example, in many cases, the additional record keeping involves having to keep track of all of the additional surgical procedures performed on a patient, capturing photographic evidence of all of the additional surgical procedures, and keeping track of timestamps associated with when all of the additional surgical procedure were performed and when the photographic evidence was taken. In some embodiments, having to perform all of this additional record keeping may result in a surgeon having to continually interrupt surgery to ensure that all of the necessary information (e.g., list of surgical procedures performed, photographic evidence, timestamps, etc.) is collected, which negatively affects efficiency associated with the surgery. In some embodiments, if the surgeon were to wait until after the surgery is complete, there may be instances in which certain information (e.g., billing codes) is forgotten and not properly documented, which can lead to requests for the additional reimbursement from the insurance companies being denied. Additionally, in some embodiments, this additional record keeping may lead to additional fees being charged to the patient to compensate for the additional time required to perform the additional record keeping.

As discussed, existing systems, however, are not configured to automatically track surgical procedures. In particular, existing systems are not able to receive input data from a variety of input sources, integrate them to make the input data suitable for annotation and inference, annotate the input data, and/or output a unique identifier associated with the surgical procedure or a segment thereof.

Accordingly, aspects of the present disclosure provide techniques for automatically tracking surgical procedures performed on a patient. For example, in some embodiments, such techniques may include the use of a digital awareness system (e.g., digital awareness system 100) to automatically generate, based at least in part on imaging data, a unique identifier corresponding to at least one surgical procedure performed on a patient's eye. In some embodiments, these techniques may involve training one or more artificial intelligence and/or ML models to take input data (e.g., input data 102, including imaging data, such as image frames and video data) and output a unique identifier associated with a surgical procedure. A variety of approaches may be used for training such ML models. For example, in some embodiments, one or more ML/AI models may be trained, based on historical patient population data to, to take input data associated with a patient's operation and output unique identifier(s) (e.g., billing code) for at least one surgical procedure performed as part of the patient's operation. In certain embodiments, the historical patient population data may refer to or include a training dataset that includes a plurality of training data entries or records, each including various types of input data (e.g., video and/or image data relating to various surgical procedures) associated with a historical patient's operation as well as a label associated with the surgical procedure performed on the historical patient. For example, the label may indicate a unique identifier (e.g., billing codes) corresponding to the surgical procedure.

Additionally, in some embodiments, photographic evidence (e.g., an image frame or video clip) of the video data that demonstrates performance of the at least one surgical procedure may be selected and included in a medical record associated with the patient along with timestamp information and the generated unique identifier. The medical record may then be automatically sent to an EMR database associated with the patient's insurance company.

Accordingly, these techniques provide a technical solution to the technical problem associated with the existing system, such as the existing systems' inability to automatically track surgical procedures, using input data (e.g., vide data), from a variety of input sources. As an additional benefit, these techniques may also reduce the amount of time and effort associated with performing additional record keeping to document surgical procedures performed on a patient. Reducing the amount of time and effort associated with performing additional record keeping allows the surgeon to focus their attention on performing surgery rather than record keeping, increasing efficiency of the surgery and reducing the chances of injury to the patent. Further, reducing the amount of time and effort associated with performing additional record keeping may lead to lower fees being passed on to the patients. Moreover, these techniques may reduce the occurrence of clerical errors when performing the additional record keeping, thereby reducing the changes that requests for additional reimbursement from insurance companies being denied.

FIG. 2 illustrates operations 200 for use by an ophthalmic surgical system, such as a digital awareness system (e.g., digital awareness system 100), for automatically tracking surgical procedures performed on a patient's eye or any other anatomical object. Operations 200 may be performed by at least one processor in one or more of computing devices(s) 120, one or more of imaging systems 110, 114, and, 116 and surgical systems 112, or any combination thereof.

As shown, operations 200 begin at step 210 with the digital awareness system obtaining input data (e.g., input data 102) associated with a surgical procedure performed on a patient's eye. As discussed, input data 102 includes data points obtained from a variety of systems and databases (e.g., systems 110-116, database 135, etc.). As an example, the input data 102 may include, for example, the imaging data captured during the surgical procedure by, for example, an intra-op imaging system 114, surgical instrument and/or usage information for the at least one surgical procedure, voice command information (e.g., requests for certain surgical instruments and/or drugs) associated with the at least one surgical procedure, surgical instrument and/or drug preparation information for the at least one surgical procedure, overall flow or progression information associated with the at least one surgical procedure, and a target surgical site (e.g., retina vs. lens) of the at least one surgical procedure. In certain embodiments, the input data 102 obtained and processed at the detection layer 121 may be further processed by the integration layer 122. Operations of the integration layer 122 were described above and are omitted here for brevity.

Thereafter, in step 220, the digital awareness system automatically generates a unique identifier corresponding to the surgical procedure performed on the eye. In some embodiments, the unique identifier may be generated by the annotation layer 123 and/or the inference layer 124 based on input data 102 received at the detection layer 121 and/or further processed by the integration layer 122.

In some embodiments, the annotation layer 123 and/or the inference layer 124 may use one or more ML/AI models (e.g., ML/AI models 127 illustrated in FIG. 1) to take the input data, such as the imaging data, and to provide one or more outputs (e.g., outputs 141-144 illustrated in FIG. 1) based on the input data. For example, in some embodiments, the one or more ML/AI models may be trained to generate and output unique identifiers for one or more surgical procedures (e.g., procedure identifier 141 illustrated in FIG. 1) performed, as reflected in the input data 102. In some embodiments, the one or more ML/AI models may be trained to identify the surgical procedures performed on the patient's eye, as reflected by the input data 102 and to output unique identifiers of the identified surgical procedures in the input data 102. As noted above, the input data 102, which may be used by the one or more ML/AI models to identify the surgical procedures, may include various types of information, such as pre-op data 104, intra-op data 106, and post-op data 108. In some embodiments, the pre-op data 104 may include one or more relevant physiological measurements for the patient (e.g., age, height, weight, body mass index, genetic makeup, race, ethnicity, sex, blood pressure, other demographic and health related information, and/or the like), relevant risk factors (e.g., smoking history, diabetes, heart disease, other underlying conditions, prior surgeries, and/or the like and/or a family history for one or more of these risk factors), medication history of the patient (e.g., current medications, past medications, allergies to medications, and the like), etc. The intra-op data 106 may include information, such as the imaging data, surgical system data (e.g., system parameters, active settings, and UI/UX/control status), other data modality (e.g., voice commands, gesture-based commands, or commands that can be received by tracking eye gaze of the surgeon), patient monitoring information (e.g., eye position), machine settings (e.g., fluidic settings, an intraocular pressure setting, a phaco energy setting, a laser power setting, a laser intensity setting, a total laser energy applied setting, etc.). The post-op data 108 may include post-operative images, measurements, patient outcome data (e.g., satisfaction score), treatment efficacy, treatment related safety endpoints, and the like.

As noted above, the one or more ML/AI models may be used to identify surgical procedures performed on a patient's eye based on a variety of the input data 102, such as a patient's medication history. In particular, some medications may increase the chances of certain conditions that require certain surgical procedures to be performed. For example, floppy iris syndrome in which an iris of a patient's eye will not dilate chemically, is often times linked to a medication used to treat enlarged prostate. In such cases, surgeons may perform a surgical procedure to insert iris hooks or a Malyugin ring to manually open a patient's iris that will not dilate chemically. Accordingly, in some embodiments, when the medication history of the patient includes an indication of a medication used to treat an enlarged prostate, the one or more ML/AI models may use this information to more accurately predict whether a Malyugin ring insertion procedure has been performed on the patient. For example, the one or more ML/AI models may combine this medication history with the imaging data (e.g., surgical instruments or implants identified in the imaging data, as described below in relation to FIGS. 3A-3D) to predict that the Malyugin ring insertion procedure has been performed on the patient.

In some embodiments, a model trainer of the digital awareness system (e.g., model trainer 126) may be configured to use a training dataset to train the one or more ML/AI models. In some embodiments, the training dataset may associate various types of information relating to various surgical procedures (e.g., input data 102) with corresponding unique identifiers. For example, the training dataset may include a plurality of data entries or records associated with various historical patients, where each data record includes various types of input data (e.g., video and/or image data relating to various surgical procedures) associated with a historical patient's operation as well a label associated with the surgical procedure performed on the historical patient. For example, the label may indicate a unique identifier (e.g., billing codes) corresponding to the surgical procedure.

As discussed, the various types of information relating to various surgical procedures performed on historical patients may include, for example, historic imaging data of the various surgical procedures, historic surgical instrument usage information during the various surgical procedures, historic voice command information (e.g., requests for certain surgical instruments and/or drugs) during various surgical procedures, historic surgical instrument and/or drug preparation information for the various surgical procedures, historic overall flow or progression of the various surgical procedures, and historic target surgical sites of the various surgical procedures.

To ensure an ML/AI model makes accurate predictions, the model trainer of the digital awareness system runs many samples in the corresponding training dataset until the prediction error is minimized. For example, in embodiments where a model is trained to identify a surgical procedure performed on a patient (e.g., phaco-emulsification, vitrectomy, procedure for stabilizing the capsular bag, a procedure to manually open the iris, etc.), the model trainer runs many samples in the corresponding training dataset to generate one or more unique identifiers (i.e., $\hat{Y}$) associated with the various surgical procedures represented in the training dataset. The model trainer is configured to train the one or more ML/AI models based on a resulting error (i.e., $Y-\hat{Y}$) for each sample, which refers to the difference between a unique identifier predicted by the ML models (i.e., $\hat{Y}$) and the actual unique identifier (i.e., $Y$) associated with a surgical procedure, as indicated by each training sample in the training dataset. In other words, the model trainer may adjust the weights of the ML/AI model to minimize the error (or divergence) between the predicted unique identifiers and the actual unique identifiers for the various surgical procedures in the training dataset. The model trainer may similarly train other ML models described herein. For example, in certain embodiments, the model trainer may train the one or more ML/AI models for identifying objects in video and/or image data.

By running many samples through the one or more ML/AI models and continuing to adjust the weights, after a certain point, the one or more ML/AI models begin making very accurate predictions with a very low error rate. At that point, the one or more ML/AI models may be ready to be deployed for taking a set of inputs (e.g., input data 102, such as imaging data, voice commands, surgical instrument usage, target surgical sites, etc.) for a current patient and generating one of the outputs described above (e.g., predicting unique identifiers for one or more procedures performed on the current patient, objects identified in video/image data).

An illustrative example of a ML/AI model trained to make predictions about a surgical procedure performed on a patient will now be described below in reference to FIGS. 3A-3D. As noted above, one or more ML/AI models may be trained to identify a surgical procedure reflected in the imaging data obtained in step 210. For example, in some embodiments, one or more ML/AI models of the digital awareness system may be configured to automatically identify at least one of one or more surgical instruments or surgical products used on the patient's eye in the imaging data. In some embodiments, the digital awareness system may then be configured to automatically identify the at least one surgical procedure based on the surgical instrument or product identified in the imaging data.

In some embodiments, in order to automatically identify the surgical procedure, an ML/AI model may be further configured to generate a confidence score associated with the surgical procedure in the imaging data. In some embodiments, the confidence score indicates a level of confidence that the identification of the surgical procedure performed in the imaging data is correct. In some embodiments, the digital awareness system may be configured to identify the surgical procedure based on the confidence score being greater than or equal to a confidence threshold. In some embodiments, as explained below, the confidence score may be determined based on or take into account one or more surgical instruments or surgical products used on the patient's eye in the imaging data. In some embodiments, as explained below, the confidence score may take into account other information related to the surgical procedure being performed, such as a target surgical site of the patient's eye.

Figure 3A:
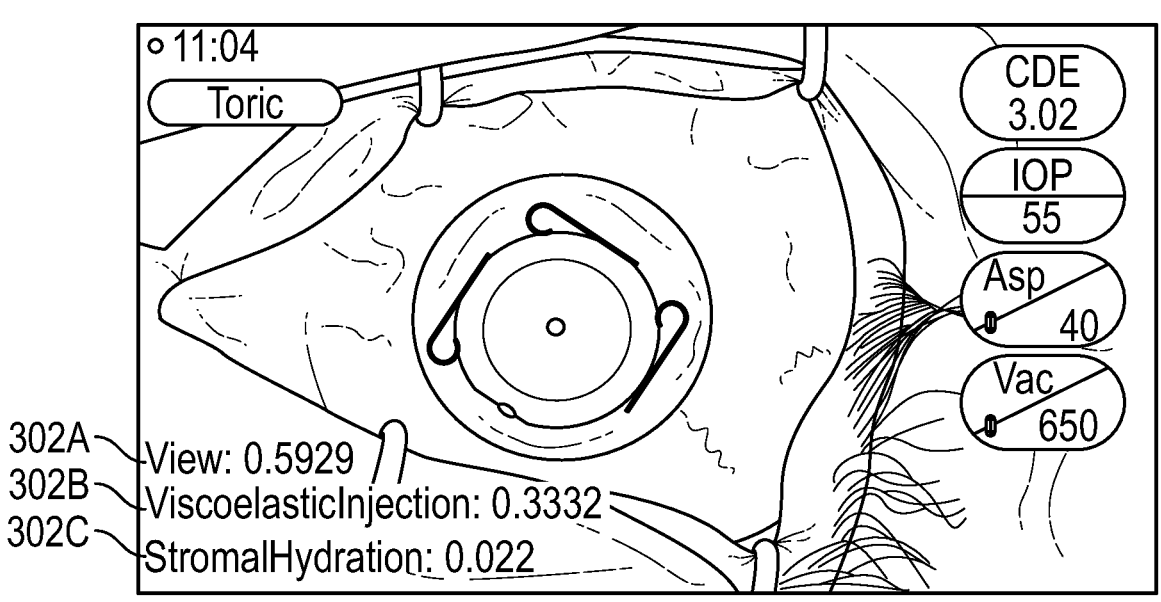
FIGS. 3A, 3B, 3C, and 3D show a plurality of image frames of imaging data representative of various surgical procedures performed on a patient's eye, in accordance with certain embodiments.

FIGS. 3A-3D show a plurality of image frames of the imaging data illustrating various surgical procedures performed on the patient's eye during cataract surgery and corresponding confidence scores generated by one or more ML/AI models 127 of the digital awareness system 100. For example, FIG. 3A illustrates a first image frame 301 of the imaging data. As shown, the first image frame 301 is merely a view of the patient's eye, lacking any surgical instruments. As such, no surgical instruments is identified by the one or more ML/AI models, resulting in the one or more ML/AI models generating a highest confidence score associated with a view of the patient's eye. For example, as shown in FIG. 3A, the one or more ML/AI models may generate a plurality of confidence scores associated with different surgical procedures. For example, the one or more ML/AI models may generate a first confidence score 302A (e.g., 0.5929) associated with a view of the patient's eye, a second confidence score 302B (e.g., 0.3332) associated with a viscoelastic injection procedure, and a third confidence score 302C (e.g., 0.022) associated with a stromal hydration procedure. Because the first confidence score 302 is higher than the second confidence score 302B and third confidence score 302C, the one or more ML/AI models may identify that only a view of the patient's eye is occurring in FIG. 3A rather than the viscoelastic injection procedure or stromal hydration procedure being performed on the patient's eye.

Figure 3B:
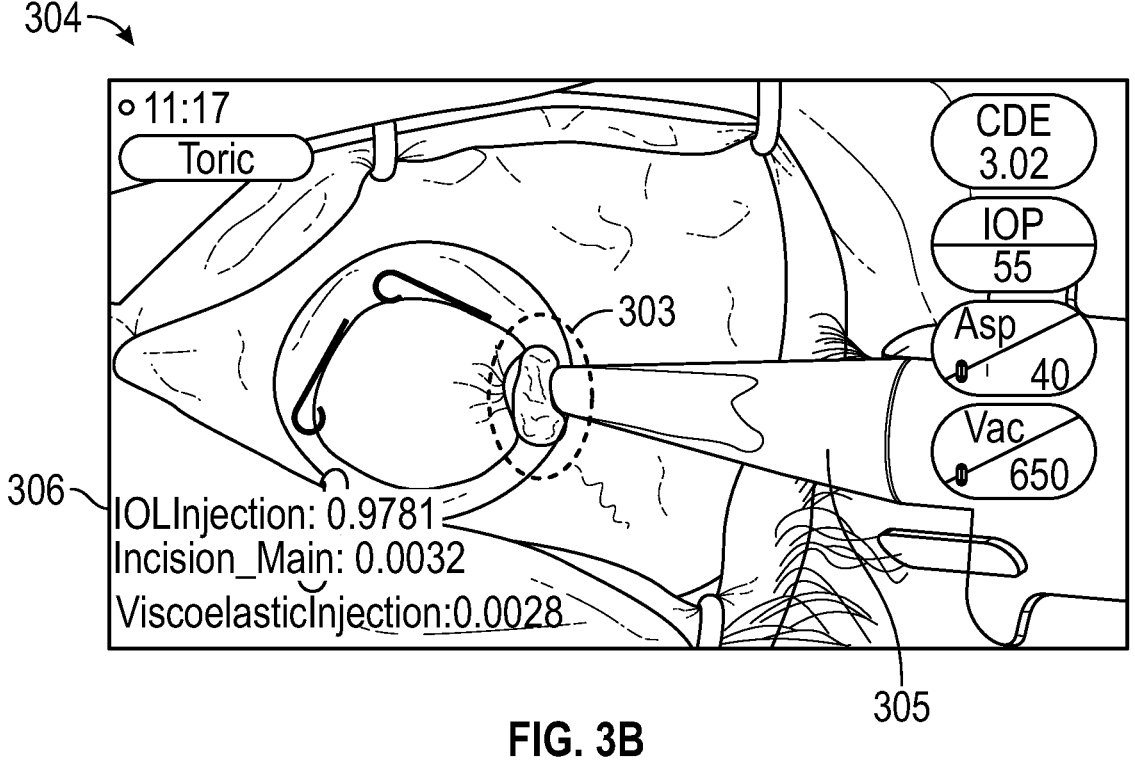

Thereafter, as illustrated in a second image frame 304 in FIG. 3B, an IOL injector 305 comes into view, which may be identified by the one or more ML/AI models. The IOL injector 305 may be used by a surgeon to perform an IOL injection procedure in which an IOL is injected into the patient's eye. Accordingly, based, at least in part, on the identified IOL injector 305, the one or more ML/AI models can predict that an IOL injection procedure is being performed in the second image frame 304. For example, the one or more ML/AI models may generate a confidence score 306 (e.g., 0.9781) associated with the IOL injection procedure based, at least partially, on the identified IOL injector 305. Thereafter, the one or more ML/AI models may predict that the IOL injection procedure is being performed in the second image frame 304 because the confidence score 306 (e.g., 0.9781) associated with the IOL injection procedure is greater than a confidence threshold (e.g., 0.50 or 50%). While 50% is used as a confidence threshold in this example, other confidence thresholds may be selected and used.

In some embodiments, information about a target surgical site, on which the one or more surgical instruments or one or more surgical products are used, may also be used by the one or more ML/AI models to generate the confidence score 306 and identify the surgical procedure performed on the eye. For example, as shown in FIG. 3B, the one or more ML/AI models may identify that the IOL injector 305 is being used on a target surgical site 303 of the patient's eye, such as an edge of a cornea of the patient's eye. This additional information related to the target surgical site 303 may be used to improve the confidence score 306, allowing the one or more ML/AI models to more accurately predict that the IOL injection procedure is being performed in the second image frame 304.

Figure 3C:
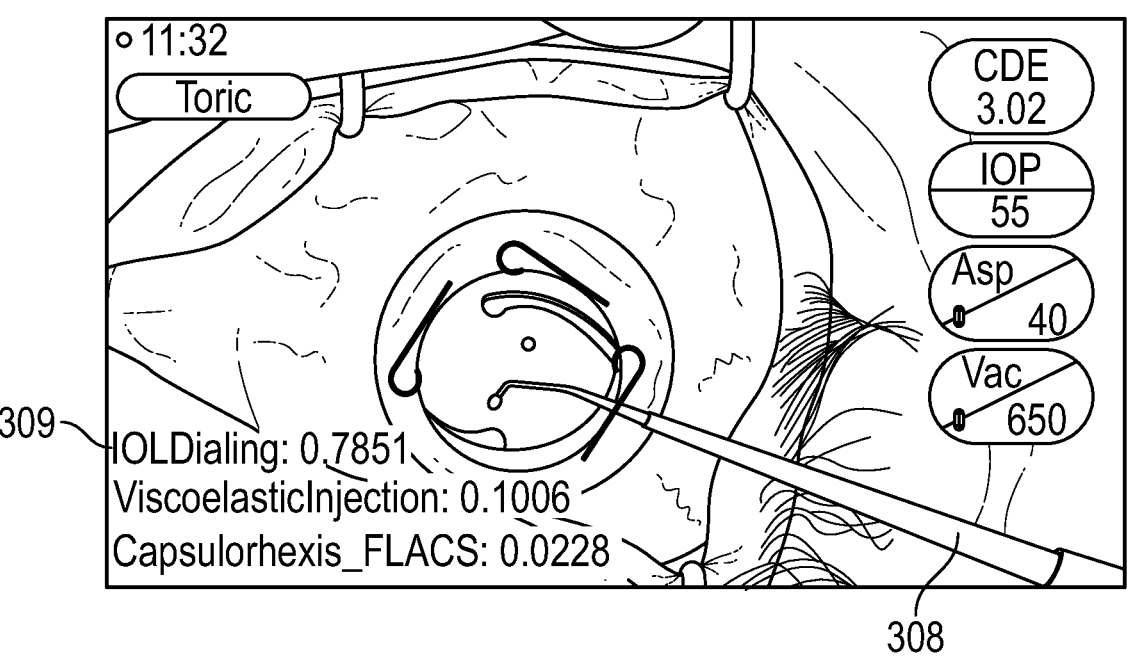

Thereafter, as illustrated in a third image frame 307 in FIG. 3C, after the IOL has been injected into the patient's eye, a Sinskey hook 308 comes into view, which may be identified by the one or more ML/AI models. The Sinskey hook 308 may be used by the surgeon to perform an IOL dilating procedure. Accordingly, based, at least in part, on the Sinskey hook 308, the one or more ML/AI models predict that the IOL dilation procedure is being performed in the third image frame 307. For example, the one or more ML/AI models may generate a confidence score 309 (e.g., 0.7851) associated with the IOL dilation procedure based, at least partially, on the identified Sinskey hook 308. Thereafter, the one or more ML/AI models may predict that the IOL dilation procedure is being performed in the third image frame 307 because the confidence score 309 (e.g., 0.7851) associated with the IOL dilation procedure is greater than a confidence threshold (e.g., 0.50 or 50%).

In some embodiments, in addition to the identified Sinskey hook 308, the one or more ML/AI models may generate the confidence score 309 and predict that the IOL dilation procedure is being performed in the third image frame 307 based on additional input information (e.g., additional intraop data 106), such as voice command information (e.g., a request for the Sinskey hook 308), surgical instrument and/or drug preparation information in the patient's medical record (e.g., indicating that the Sinskey hook 308 was prepared for surgery), and an overall flow or progression of the cataract surgery. For example, cataract surgery may generally have a known procedural flow that indicates that an IOL dilation procedure will be performed after the IOL injection procedure. As such, after identifying performance of the IOL injection procedure, the one or more ML/AI models may generate the confidence score 309 based on the overall procedural flow of cataract surgery and, thereafter, predict or identify that the IOL dilation procedure is being performed in the third image frame 307.

Figure 3D:
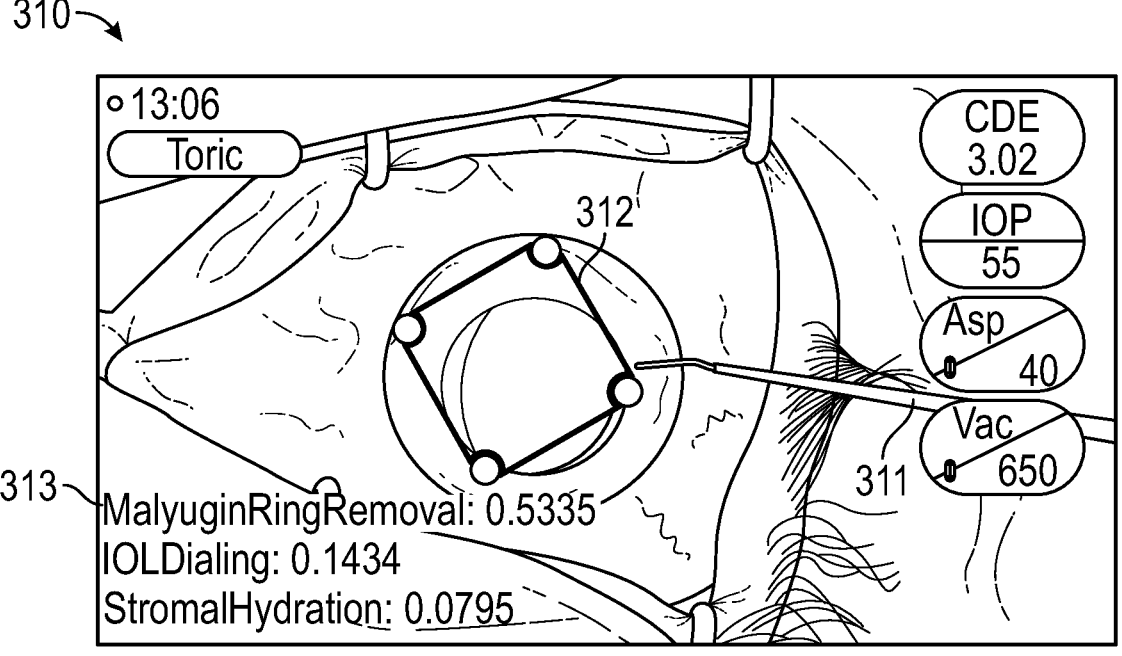

After the IOL dilation procedure, as illustrated in a fourth image frame 310 in FIG. 3D, a Sinskey hook 311 comes into view, which may be identified by the one or more ML/AI models. Additionally, the one or more ML/AI models may identify a Malyugin ring 312 in the fourth image frame 310. In some embodiments, the Sinskey hook 311 may be used by the surgeon to perform a Malyugin ring removal procedure in order to remove the Malyugin ring 312 from the patient's eye after the IOL is placed. Accordingly, based, at least in part, on the identified Sinskey hook 311 and Malyugin ring 312, the one or more ML/AI models predict that the Malyugin ring removal procedure is being performed in the fourth image frame 310. For example, the one or more ML/AI models may generate a confidence score 313 (e.g., 0.5335) associated with the Malyugin ring removal procedure based, at least partially, on the identified Sinskey hook 311. Thereafter, the one or more ML/AI models may predict that the Malyugin ring removal procedure is being performed in the fourth image frame 310 because the confidence score 313 (e.g., 0.5335) associated with the Malyugin ring removal procedure is greater than a confidence threshold (e.g., 0.50 or 50%).

In some embodiments, the one or more ML/AI models may include a deep learning (DL) model that may be trained to predict a surgical procedure based on video and/or image data, such as the plurality of image frames of the imaging data illustrated in FIGS. 3A, 3B, 3C, and 3D. The DL model may implicitly identify an instrument used in the video/image data and encode features of the identified instruments. In some embodiments, the DL model may be trained to identify other features within the video/image data and make a prediction regarding a surgical procedure that is being performed, such as the motion of a particular instrument identified in the video/image data, a temporal sequence of actions in the video/image data, a presence of certain object in the eye (e.g., IOL and IOL haptics), a temporal sequence of current procedure to the preceding procedures (such as after IOL injection).

In some embodiments, the one or more ML/AI models may include an ML model that is configured to make a prediction regarding a surgical procedure that is being performed based on a detected a combination of features within video and/or image data (e.g., the plurality of image frames of the imaging data illustrated in FIGS. 3A, 3B, 3C, and 3D). In some embodiments, the combination of features that may be used by the ML model may include the presence of an IOL, the presence of particular instruments, the motion of the instrument, or the temporal sequence of current procedure to the preceding procedures (such as after IOL injection), and use those features to make prediction regarding a surgical procedure that is being performed.

Once a surgical procedure has been identified using the techniques described above, the digital awareness system may generate a unique identifier corresponding to the surgical procedure, as noted above with respect to step 220 in FIG. 2. Thereafter, in step 230, the digital awareness system automatically provides visual representation (e.g., visual assistance 144 illustrated in FIG. 1) associated with the surgical procedure and the generated unique identifier on a user interface of or associated with the digital awareness system. In some embodiments, to ensure that the correct unique identifier is generated for the surgical procedure, the visual representation provided (e.g., displayed) on the user interface may allow a user of the digital awareness system to either confirm or deny the unique identifier generated for the at least one surgical procedure.

Thereafter, in some embodiments, as illustrated in step 240 of FIG. 2, upon receiving a confirmation from the user (e.g., a surgeon or their medical staff) that the unique identifier (e.g., confirming that the unique identifier is correct) is correct, the digital awareness system may automatically transmit the unique identifier to another system, such as an EMR system (e.g., database 135), for automatic processing. In some embodiments, as illustrated in step 250 of FIG. 2, upon receiving user input contradicting or rejecting the unique identifier, the digital awareness system may automatically override the unique identifier and transmit a second unique identifier provided by the user through the user interface to the EMR for automatic processing.

In some embodiments, in addition to transmitting the unique identifier to the EMR system, other information associated with the identified surgical may be provided to the EMR system as well. For example, in some embodiments, the digital awareness system may be configured to select and output at least one of a representative image frame or a representative video clip that demonstrates performance of the surgical procedure (e.g., representative image/video 142 illustrated in FIG. 1). In some embodiments, the digital awareness system may select the representative image frame or the representative video clip based on a confidence score, such as the confidence scores illustrated in FIGS. 3A-3D, being greater than or equal to a confidence threshold. For example, the confidence score may indicate a level of confidence that the surgical procedure is demonstrated in the selected representative image frame or representative video clip. Thereafter, the digital awareness system may automatically transmit, to the EMR system, at least one of the representative image frame or the representative video clip that demonstrates performance of the surgical procedure. In some embodiments, the digital awareness system may report some summative metrics to the EMR, or directly to surgeons, such as a time duration that each surgical procedure takes.

In some embodiments, in order to automatically transmit the unique identifier and at least one of the representative image frame or the representative video clip to the EMR system, the digital awareness system may generate a patient record and transmit the patient record to the EMR system. The patient record may include an indication of the identified surgical procedure, the unique identifier corresponding to the surgical procedure, and at least one of the representative image frame or the representative video clip that demonstrates performance of the surgical procedure. In some embodiments, the digital awareness system may also be configured to output and include, in the patent record, a time-stamp (e.g., timestamp information 143 illustrated in FIG. 1) indicating when the representative image frame or representative video clip was captured.

In some embodiments, the digital awareness system may also be configured to allow the user to confirm or deny the representative image frame or video clip. For example, in some embodiments, the digital awareness system may transmit the representative image frame or video clip to the EMR system, only if the user confirms that the representative image frame or video clip is correct. In other cases, upon receiving user input contradicting or rejecting the representative image frame or representative video clip, the digital awareness system may be configured to automatically override the representative image frame or representative video clip and allow the user to find or select a second representative image frame or video clip. For example, the digital awareness system may transmit a second representative image frame or representative video clip, provided by the user through the user interface, to the second apparatus for automatic processing.

Figure 4:
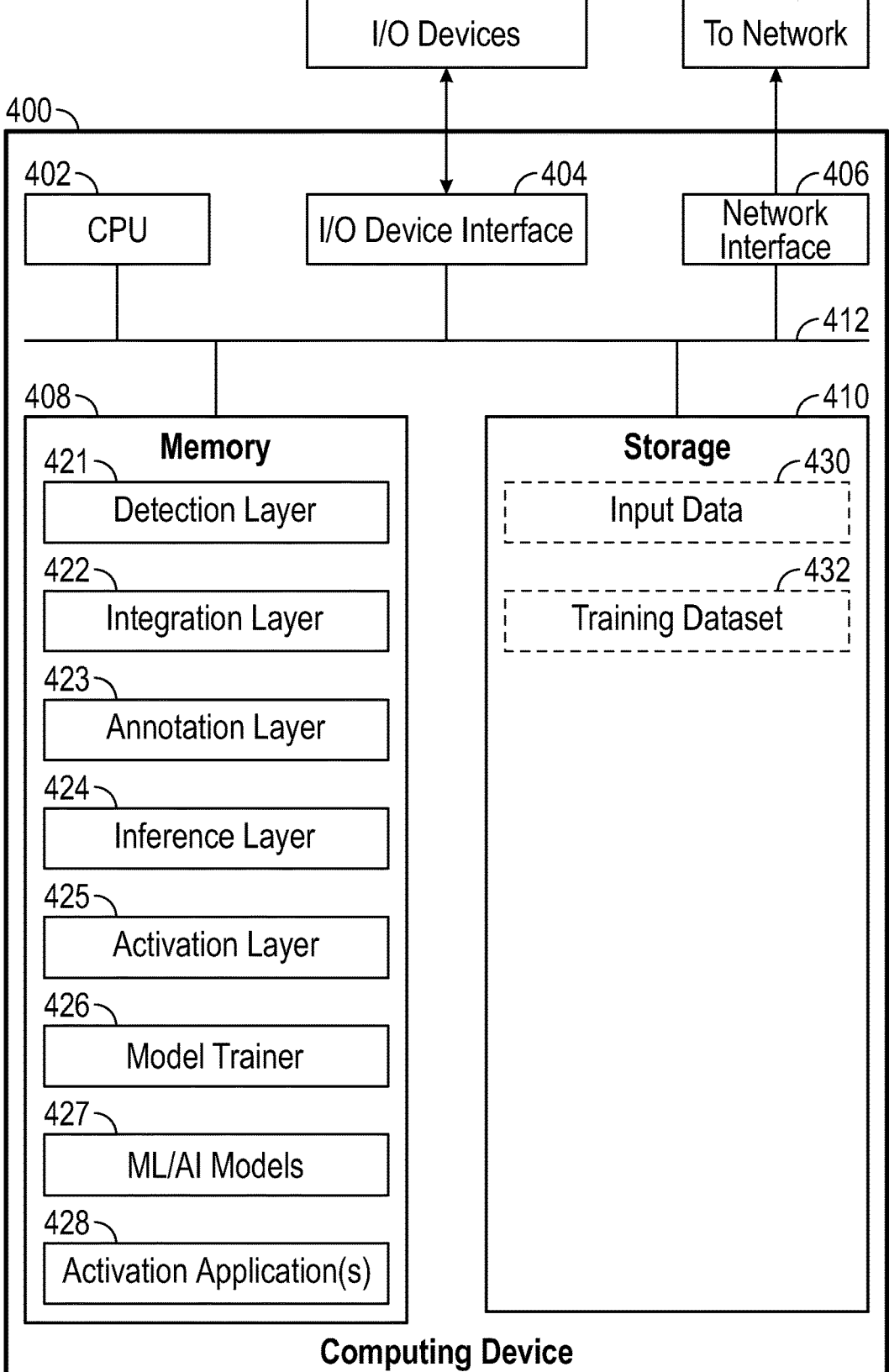
FIG. 4 illustrates an example computing apparatus, in accordance with certain embodiments.

FIG. 4 illustrates an example digital awareness system 400 that implements, at least partly, one or more functionalities of a digital awareness system (e.g., digital awareness system 100), such as the operations 200 illustrated in FIG.

2. Digital awareness system 400 may be any one of imaging systems 110, 114, 116, surgical systems 112, and computing devices 120 of FIG. 1.

As shown, digital awareness system 400 includes a central processing unit (CPU) 402, one or more I/O device interfaces 404, which may allow for the connection of various I/O devices 414 (e.g., keyboards, displays, mouse devices, pen input, etc.) to the digital awareness system 400, network interface 406 through which digital awareness system 400 is connected to network 490 (which may be a local network, an intranet, the internet, or any other group of computing systems communicatively connected to each other, as described in relation to FIG. 1), a memory 408, storage 410, and an interconnect 412.

In cases where digital awareness system 400 is an imaging system (e.g., imaging system 110, 114, or 116), digital awareness system 400 may further include one or more optical components for obtaining ophthalmic imaging of a patient's eye as well as any other components known to one of ordinary skill in the art. In cases where digital awareness system 400 is a surgical system (e.g., surgical systems 112), digital awareness system 400 may further include many other components known to one of ordinary skill in the art to perform the ophthalmic surgeries described above in relation to FIG. 1 and known to one of ordinary skill in the art.

CPU 402 may retrieve and execute programming instructions stored in the memory 408. Similarly, CPU 402 may retrieve and store application data residing in the memory 408. The interconnect 412 transmits programming instructions and application data, among CPU 402, I/O device interfaces 404, network interface 406, memory 408, and storage 410. CPU 402 is included to be representative of a single CPU, multiple CPUs, a single CPU having multiple processing cores, and the like.

Memory 408 is representative of a volatile memory, such as a random access memory, and/or a nonvolatile memory, such as nonvolatile random access memory, phase change random access memory, or the like. As shown, memory 608 includes detection layer 421, integration layer 422, annotation layer 423, inference layer 424, activation layer 425, model trainer 426, ML/AI models 427, and activation application(s) 428. The functionalities of detection layer 421, integration layer 422, annotation layer 423, inference layer 424, activation layer 425, model trainer 426, ML/AI models 427 are similar or identical to the functionalities of detection layer 121, integration layer 122, annotation layer 123, inference layer 124, activation layer 125, model trainer 126, and ML/AI models 127. Note that all of the instructions, modules, layers, and applications in memory 208 are being shown in dashed boxes to show that they are optional because, depending on the functionality of digital awareness system 400 one or more of the instructions, modules, layers, and applications may be executed by digital awareness system 400 while others may not be. For example, in cases where digital awareness system 400 is an imaging system (e.g., one of imaging systems 110, 114, or 116) or a surgical system (e.g., surgical system 112), memory 408 may, in certain embodiments, store activation application(s) 428 (in order to trigger one or more actions based on outputs 140) but not model trainer 426. In cases where digital awareness system 400 is a server system (e.g., not an imaging system or surgical system) configured to train ML/AI models 427, memory 408 may, in certain embodiments, store model trainer 426 and not activation application(s) 428.

Storage 410 may be non-volatile memory, such as a disk drive, solid state drive, or a collection of storage devices distributed across multiple storage systems. Storage 410 may optionally store input data 430 (e.g., similar or identical to input data 102) as well as a training dataset 432. Training dataset 432 may be used by model trainer 426 to train ML/AI models 427 as described above. Training dataset 432 may also be stored in external storage, such as a database (e.g., database 130).

In some embodiments, one or more of the detection layer 421, integration layer 422, annotation layer 423, inference layer 424, activation layer 425, model trainer 426, ML/AI models 427, and activation application(s) 428 included within the memory 408 may include programming instructions for implementing operations 200 illustrated in FIG. 2.

For example, in some embodiments, based on the programming instructions, the CPU 402 may cause the digital awareness system 400 to obtain imaging data of a patient's eye captured during a period of time. In some embodiments, the CPU 402 may further cause the digital awareness system 400 to automatically generate a unique identifier corresponding to at least one surgical procedure performed on the patient's eye during the period of time based on the imaging data. In some embodiments, the CPU 402 may further cause the digital awareness system 400 to automatically cause a visual representation associated with the at least one surgical procedure and the generated unique identifier to be provided on a user interface (e.g., I/O devices 414, such as a display). In some embodiments, the CPU 402 may further cause the digital awareness system 400 to automatically transmit the unique identifier to a second apparatus for automatic processing upon receiving a confirmation from a user confirming the unique identifier. In some embodiments, the CPU 402 may further cause the digital awareness system 400 to, upon receiving user input contradicting or rejecting the unique identifier, automatically override the unique identifier and transmit a second unique identifier provided by the user through the user interface to the second apparatus for automatic processing.

In some embodiments, the I/O devices 414 of the digital awareness system 400 may include digital camera configured to capture the imaging data of the patient's eye during the period of time and to output the imaging data to the CPU 402.

In some embodiments, the CPU 402 may further cause the digital awareness system 400 to automatically identify at least one of: one or more surgical instruments used on the patient's eye in the imaging data; or one or more surgical products used on the patient's eye in the imaging data.

In some embodiments, the CPU 402 may further cause the digital awareness system 400 to automatically identify the at least one surgical procedure performed on the patient's eye based on at least one of the one or more surgical instruments identified in the imaging data or the one or more surgical products identified in the imaging data.

In some embodiments, in order to automatically identify the at least one surgical procedure performed on the patient's eye, the CPU 402 may cause the digital awareness system 400 to generate, based on the one or more surgical instruments identified in the imaging data or the one or more surgical products identified in the imaging data, a confidence score for the at least one surgical procedure performed on the patient's eye in the imaging data, the confidence score indicating a level of confidence that the identification of the at least one surgical procedure is correct. Additionally, the CPU 402 may cause the digital awareness system 400 to automatically identify the at least one surgical procedure performed on the patient's eye based on the confidence score.

In some embodiments, the CPU 402 may further cause the digital awareness system 400 to automatically identify the at least one surgical procedure based on the confidence score being greater than or equal to a confidence threshold for at least a threshold amount of time.

In some embodiments, the CPU 402 may further cause the digital awareness system 400 to automatically identify, in the imaging data, a target surgical site of the eye on which the one or more surgical instruments or one or more surgical products are used. In some embodiments, the CPU 402 may further cause the digital awareness system 400 to automatically identify the at least one surgical procedure performed on the patient's eye further based on the target surgical site of the patient's eye identified in the imaging data.

In some embodiments, the CPU 402 may further cause the digital awareness system 400 to automatically identify the at least one surgical procedure based on the ML/AI models 427 trained to identify surgical procedures performed in the imaging data.

In some embodiments, the CPU 402 may further cause the digital awareness system 400 to automatically generate the unique identifier corresponding to the at least one surgical procedure based on the ML/AI models 427 trained to generate unique identifiers for surgical procedures performed in the imaging data.

In some embodiments, the CPU 402 may further cause the digital awareness system 400 to obtain the training dataset 432. In some embodiments, the training dataset 432 associates a historical imaging data relating to various surgical procedures with corresponding unique identifiers. In some embodiments, the CPU 402 may further cause the model trainer 426 of the digital awareness system 400 to train the ML/AI models 427 based on the training dataset to generate, based on the imaging data, the unique identifier corresponding to the at least one surgical procedure.

In some embodiments, the imaging data comprises a plurality of image frames captured during the period of time. In some embodiments, the CPU 402 may further cause the digital awareness system 400 to select at least one of a representative image frame or a representative video clip that demonstrates performance of the at least one surgical procedure. In some embodiments, the CPU 402 may further cause the digital awareness system 400 to select at least one of the representative image frame or the representative video clip based on a confidence score being greater than or equal to a confidence threshold. In some embodiments, the confidence score indicating a level of confidence that the at least one surgical procedure is demonstrated in the selected representative image frame or representative video clip.

In some embodiments, the CPU 402 may further cause the digital awareness system 400 to automatically transmit, to the second apparatus, at least one of the representative image frame or the representative video clip that demonstrates performance of the at least one surgical procedure.

In some embodiments, in order to automatically transmit the unique identifier and at least one of the representative image frame or the representative video clip to the second apparatus, the CPU 402 may further cause the digital awareness system 400 to generate a patient record. In some embodiments, the patient record includes an indication of the at least one surgical procedure, the unique identifier corresponding to the at least one surgical procedure, and at least one of the representative image frame or the representative video clip that demonstrates performance of the at least one surgical procedure.

In some embodiments, the CPU 402 may further cause the digital awareness system 400 to include in the patent record a time-stamp indicating when the representative image frame or representative video clip was captured.

In some embodiments, the visual representation provided on the user interface (e.g., I/O devices 414, such as a display) further includes the selected representative image frame or representative video clip. In such cases, in order to automatically transmit the representative image frame or representative video clip to the second apparatus, the CPU 402 may further cause the digital awareness system 400 to transmit the representative image frame or representative video clip to the second apparatus for automatic processing upon receiving a confirmation from a user confirming the unique identifier, automatically. In some embodiments, the CPU 402 may further cause the digital awareness system 400 to, upon receiving user input contradicting or rejecting the representative image frame or representative video clip, automatically override the representative image frame or representative video clip and transmit a second representative image frame or representative video clip, provided by the user through the user interface, to the second apparatus for automatic processing.

ADDITIONAL EXAMPLE EMBODIMENTS

Additional implementation examples are described in the following numbered embodiments:

Embodiment 1: A an ophthalmic surgical system for automatically tracking surgical procedures, comprising: a memory comprising executable instructions; and a processor configured to execute the executable instructions and cause the ophthalmic surgical system to: obtain imaging data of one or more of: patient anatomy observed during at least one surgical procedure, one or more surgical instruments observed during the at least one surgical procedure, or surgical implants observed during the at least one surgical procedure; automatically generate a unique identifier corresponding to at least one aspect of the at least one surgical procedure based on the imaging data; and automatically transmit the unique identifier to a second apparatus for processing.

Embodiment 2: The ophthalmic surgical system of Embodiment 1, wherein the imaging data comprises at least one of video data or image frames.

Embodiment 3: The ophthalmic surgical system of Embodiment 1, wherein the at least one processor is further configured to cause the ophthalmic surgical system to automatically cause a visual representation associated with the at least one surgical procedure and the generated unique identifier to be stored in the memory.

Embodiment 4: The ophthalmic surgical system of Embodiment 1, wherein the ophthalmic surgical system further comprises a digital camera configured to: capture the imaging data of the patient anatomy during a period of time; and output the imaging data to the at least one processor.

Embodiment 5: The ophthalmic surgical system of Embodiment 1, wherein the at least one processor is further configured to cause the ophthalmic surgical system to automatically identify the at least one surgical procedure based on imaging data.

Embodiment 6: The ophthalmic surgical system of Embodiment 5, wherein, in order to identify the at least one surgical procedure, the processor is further configured to cause the ophthalmic surgical system to automatically identify at least one of: the one or more surgical instruments in the imaging data; or the one or more surgical implants in the imaging data.

Embodiment 7: The ophthalmic surgical system of Embodiment 6, wherein the at least one processor is further configured to cause the ophthalmic surgical system to automatically identify the at least one surgical procedure based on at least one of the one or more surgical instruments identified in the imaging data or the one or more surgical products identified in the imaging data.

Embodiment 8: The ophthalmic surgical system of Embodiment 7, wherein, in order to automatically identify the at least one surgical procedure, the at least one processor is configured to cause the ophthalmic surgical system to: generate, based on the one or more surgical instruments identified in the imaging data or the one or more surgical products identified in the imaging data, a confidence score for the at least one surgical procedure, the confidence score indicating a level of confidence that the identification of the at least one surgical procedure is correct; and automatically identify the at least one surgical procedure based on the confidence score.

Embodiment 9: The ophthalmic surgical system of Embodiment 8, wherein the processor is further configured to cause the ophthalmic surgical system to automatically identify the at least one surgical procedure based on the confidence score being greater than or equal to a confidence threshold for at least a threshold amount of time.

Embodiment 10: The ophthalmic surgical system of Embodiment 6, wherein the at least one processor is further configured to cause the ophthalmic surgical system to: automatically identify, in the imaging data, a target surgical site of the anatomical object on which the one or more surgical instruments or one or more surgical products are used; and automatically identify the at least one surgical procedure further based on the target surgical site of the anatomical object identified in the imaging data.

Embodiment 11: The ophthalmic surgical system of Embodiment 5, wherein the at least one processor is configured to cause the ophthalmic surgical system to automatically identify the at least one surgical procedure based on a machine learning (ML) model trained to identify surgical procedures performed in the imaging data.

Embodiment 12: The ophthalmic surgical system of Embodiment 1, wherein the at least one processor is configured to cause the ophthalmic surgical system to automatically generate the unique identifier corresponding to the at least one surgical procedure based on machine learning (ML) model trained to generate unique identifiers for surgical procedures performed in the imaging data.

Embodiment 13: The ophthalmic surgical system of Embodiment 12, wherein the at least one processor is configured to cause the ophthalmic surgical system to: obtain a training dataset, the training dataset associating historical imaging data relating to various surgical procedures with corresponding unique identifiers; and train the ML model based on the training dataset to generate, based on the imaging data, the unique identifier corresponding to the at least one surgical procedure.

Embodiment 14: The ophthalmic surgical system of Embodiment 1, wherein: the imaging data comprises a plurality of image frames captured during the period of time; and the at least one processor is further configured to cause the ophthalmic surgical system to select at least one of a representative image frame or a representative video clip that demonstrates performance of the at least one surgical procedure.

Embodiment 15: The ophthalmic surgical system of Embodiment 14, wherein the at least one processor is configured to select at least one of the representative image frame or the representative video clip based on a confidence score being greater than or equal to a confidence threshold, the confidence score indicating a level of confidence that the at least one surgical procedure is demonstrated in the selected representative image frame or representative video clip.

Embodiment 16: The ophthalmic surgical system of Embodiment 14, wherein the at least one processor is further configured to cause the ophthalmic surgical system to automatically transmit, to the second apparatus, at least one of the representative image frame or the representative video clip that demonstrates performance of the at least one surgical procedure.

Embodiment 17: The ophthalmic surgical system of Embodiment 16, wherein: in order to automatically transmit the unique identifier and at least one of the representative image frame or the representative video clip to the second apparatus, the at least one processor is further configured to cause the ophthalmic surgical system to generate a patient record; and the patient record includes an indication of the at least one surgical procedure, the unique identifier corresponding to the at least one surgical procedure, and at least one of the representative image frame and the representative video clip that demonstrates performance of the at least one surgical procedure.

Embodiment 18: The ophthalmic surgical system of Embodiment 17, wherein the at least one processor is further configured to cause the apparatus to include in the patent record a time-stamp indicating when the representative image frame or representative video clip was captured.

Embodiment 19: The ophthalmic surgical system of Embodiment 16, wherein: the at least one processor is further configured to cause the ophthalmic surgical system to automatically cause a visual representation associated with the at least one surgical procedure and the generated unique identifier to be stored in the memory; the visual representation stored in memory further includes the selected representative image frame or representative video clip; and in order to automatically transmit the representative image frame or representative video clip to the second apparatus, the at least one processor is further configured to: upon receiving a confirmation from a user confirming the unique identifier, automatically transmit the representative image frame or representative video clip to the second apparatus for automatic processing; and upon receiving user input contradicting or rejecting the representative image frame or representative video clip, automatically override the representative image frame or representative video clip and transmit a second representative image frame or representative video clip, provided by the user through the user interface, to the second apparatus for automatic processing.

ADDITIONAL CONSIDERATIONS

The preceding description is provided to enable any person skilled in the art to practice the various embodiments described herein. Various modifications to these embodiments will be readily apparent to those skilled in the art, and the generic principles defined herein may be applied to other embodiments. For example, changes may be made in the function and arrangement of elements discussed without departing from the scope of the disclosure. Various examples may omit, substitute, or add various procedures or components as appropriate. Also, features described with respect to some examples may be combined in some other examples. For example, an apparatus may be implemented or a method may be practiced using any number of the aspects set forth herein. In addition, the scope of the disclosure is intended to cover such an apparatus or method that is practiced using other structure, functionality, or structure and functionality in addition to, or other than, the various aspects of the disclosure set forth herein. It should be understood that any aspect of the disclosure disclosed herein may be embodied by one or more elements of a claim.

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c).

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

The methods disclosed herein comprise one or more steps or actions for achieving the methods. The method steps and/or actions may be interchanged with one another without departing from the scope of the claims. In other words, unless a specific order of steps or actions is specified, the order and/or use of specific steps and/or actions may be modified without departing from the scope of the claims. Further, the various operations of methods described above may be performed by any suitable means capable of performing the corresponding functions. The means may include various hardware and/or software component(s) and/or module(s), including, but not limited to a circuit, an application specific integrated circuit (ASIC), or processor. Generally, where there are operations illustrated in figures, those operations may have corresponding counterpart means-plus-function components with similar numbering.

The various illustrative logical blocks, modules and circuits described in connection with the present disclosure may be implemented or performed with a general purpose processor, a digital signal processor (DSP), an application specific integrated circuit (ASIC), a field programmable gate array (FPGA) or other programmable logic device (PLD), discrete gate or transistor logic, discrete hardware components, or any combination thereof designed to perform the functions described herein. A general-purpose processor may be a microprocessor, but in the alternative, the processor may be any commercially available processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

A processing system may be implemented with a bus architecture. The bus may include any number of interconnecting buses and bridges depending on the specific application of the processing system and the overall design constraints. The bus may link together various circuits including a processor, machine-readable media, and input/output devices, among others. A user interface (e.g., keypad, display, mouse, joystick, etc.) may also be connected to the bus. The bus may also link various other circuits such as timing sources, peripherals, voltage regulators, power management circuits, and the like, which are well known in the art, and therefore, will not be described any further. The processor may be implemented with one or more general-purpose and/or special-purpose processors. Examples include microprocessors, microcontrollers, DSP processors, and other circuitry that can execute software. Those skilled in the art will recognize how best to implement the described functionality for the processing system depending on the particular application and the overall design constraints imposed on the overall system.

If implemented in software, the functions may be stored or transmitted over as one or more instructions or code on a computer-readable medium. Software shall be construed broadly to mean instructions, data, or any combination thereof, whether referred to as software, firmware, middleware, microcode, hardware description language, or otherwise. Computer-readable media include both computer storage media and communication media, such as any medium that facilitates transfer of a computer program from one place to another. The processor may be responsible for managing the bus and general processing, including the execution of software modules stored on the computer-readable storage media. A computer-readable storage medium may be coupled to a processor such that the processor can read information from, and write information to, the storage medium. In the alternative, the storage medium may be integral to the processor. By way of example, the computer-readable media may include a transmission line, a carrier wave modulated by data, and/or a computer readable storage medium with instructions stored thereon separate from the wireless node, all of which may be accessed by the processor through the bus interface. Alternatively, or in addition, the computer-readable media, or any portion thereof, may be integrated into the processor, such as the case may be with cache and/or general register files. Examples of machine-readable storage media may include, by way of example, RAM (Random Access Memory), flash memory, ROM (Read Only Memory), PROM (Programmable Read-Only Memory), EPROM (Erasable Programmable Read-Only Memory), EEPROM (Electrically Erasable Programmable Read-Only Memory), registers, magnetic disks, optical disks, hard drives, or any other suitable storage medium, or any combination thereof. The machine-readable media may be embodied in a computer-program product.

A software module may comprise a single instruction, or many instructions, and may be distributed over several different code segments, among different programs, and across multiple storage media. The computer-readable media may comprise a number of software modules. The software modules include instructions that, when executed by an apparatus such as a processor, cause the processing system to perform various functions. The software modules may include a transmission module and a receiving module. Each software module may reside in a single storage device or be distributed across multiple storage devices. By way of example, a software module may be loaded into RAM from a hard drive when a triggering event occurs. During execution of the software module, the processor may load some of the instructions into cache to increase access speed. One or more cache lines may then be loaded into a general register file for execution by the processor. When referring to the functionality of a software module, it will be understood that such functionality is implemented by the processor when executing instructions from that software module.

The following claims are not intended to be limited to the embodiments shown herein, but are to be accorded the full scope consistent with the language of the claims. Within a claim, reference to an element in the singular is not intended to mean "one and only one" unless specifically so stated, but rather "one or more." Unless specifically stated otherwise, the term "some" refers to one or more. No claim element is to be construed under the provisions of 35 U.S.C. § 112(f) unless the element is expressly recited using the phrase "means for" or, in the case of a method claim, the element is recited using the phrase "step for." All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims.

What is claimed is:

1. A surgical system for automatically tracking surgical procedures performed on an anatomical object of a patient, comprising:

a memory comprising executable instructions; and at least one processor configured to execute the executable instructions and cause the surgical system to:

obtain imaging data of the anatomical object of the patient captured during a period of time;

generate a confidence score indicating a level of confidence associated with at least one surgical procedure being performed on the anatomical object during the period of time, wherein the confidence score is generated based on at least one of:

one or more surgical instruments used on the anatomical object in the imaging data; or one or more surgical products used on the anatomical object in the imaging data;

automatically identify the at least one surgical procedure as being performed on the anatomical object during the period of time based on the confidence score;

responsive to the automatic identification of the at least one surgical procedure, automatically generate a unique identifier corresponding to the at least one surgical procedure;

automatically cause a visual representation associated with the at least one surgical procedure and the generated unique identifier to be provided on a user interface;

upon receiving a confirmation from a user confirming the unique identifier, automatically transmit the unique identifier to a second apparatus for automatic processing; and upon receiving user input contradicting or rejecting the unique identifier, automatically override the unique identifier and transmit a second unique identifier provided by the user through the user interface to the second apparatus for automatic processing.

2. The surgical system of claim 1, wherein the surgical system further comprises a digital camera configured to:

capture the imaging data of the anatomical object of the patient during the period of time; and output the imaging data to the at least one processor.

3. The surgical system of claim 1, wherein the at least one processor is further configured to cause the surgical system to automatically identify the at least one of:

one or more surgical instruments used on the anatomical object in the imaging data; or one or more surgical products used on the anatomical object in the imaging data.

4. The surgical system of claim 1, wherein the at least one surgical procedure is automatically identified based on the confidence score being greater than or equal to a confidence threshold for at least a threshold amount of time.

5. The surgical system of claim 1, wherein the at least one processor is further configured to cause the surgical system to:

automatically identify, in the imaging data, a target surgical site of the anatomical object on which the one or more surgical instruments or one or more surgical products are used; and automatically identify the at least one surgical procedure performed on the anatomical object further based on the target surgical site of the anatomical object identified in the imaging data.

6. The surgical system of claim 1, wherein the at least one processor is configured to cause the surgical system to automatically identify the at least one surgical procedure based on a machine learning (ML) model trained to identify surgical procedures performed in the imaging data.

7. The surgical system of claim 1, wherein the at least one processor is configured to cause the surgical system to automatically generate the unique identifier corresponding to the at least one surgical procedure based on a machine learning (ML) model trained to generate unique identifiers for surgical procedures performed in the imaging data.

8. The surgical system of claim 7, wherein the at least one processor is configured to cause the surgical system to:

obtain a training dataset, the training dataset associating historical imaging data relating to various surgical procedures with corresponding unique identifiers; and train the ML model based on the training dataset to generate, based on the imaging data, the unique identifier corresponding to the at least one surgical procedure.

9. The surgical system of claim 1, wherein:

the imaging data comprises a plurality of image frames captured during the period of time; and the at least one processor is further configured to cause the surgical system to select at least one of a representative image frame or a representative video clip that demonstrates performance of the at least one surgical procedure.

10. The surgical system of claim 9, wherein the at least one processor is configured to select the at least one of a representative image frame or a representative video clip based on a confidence score being greater than or equal to a confidence threshold, the confidence score indicating a level of confidence that the at least one surgical procedure is demonstrated in the selected at least one of a representative image frame or a representative video clip.

11. The surgical system of claim 9, wherein the at least one processor is further configured to cause the surgical system to automatically transmit, to the second apparatus, the at least one of a representative image frame or a representative video clip that demonstrates performance of the at least one surgical procedure.

12. The surgical system of claim 11, wherein:

in order to automatically transmit the unique identifier and the at least one of a representative image frame or a representative video clip to the second apparatus, the at least one processor is further configured to cause the surgical system to generate a patient record; and the patient record includes an indication of the at least one surgical procedure, the unique identifier corresponding to the at least one surgical procedure, and the at least one of a representative image frame or the representative video clip that demonstrates performance of the at least one surgical procedure.

13. The surgical system of claim 12, wherein the at least one processor is further configured to cause the surgical system to include in the patient record a time-stamp indicating when the at least one of a representative image frame or a representative video clip was captured.

14. A method for automatically tracking surgical procedures performed on an anatomical object of a patient by a surgical system, comprising:

obtaining imaging data of the anatomical object of the patient captured during a period of time;

generating a confidence score for at least one surgical procedure based on at least one of:

one or more surgical instruments used on the anatomical object in the imaging data; or one or more surgical products used on the anatomical object in the imaging data;

automatically identifying the at least one surgical procedure as being performed on the anatomical object during the period of time based on the confidence score;

responsive to the automatically identifying the at least one surgical procedure, automatically generating a unique identifier corresponding to the at least one surgical procedure;

automatically causing a visual representation associated with the at least one surgical procedure and the generated unique identifier to be provided on a user interface;

upon receiving a confirmation from a user confirming the unique identifier, automatically transmitting the unique identifier to a second apparatus for automatic processing; and upon receiving user input contradicting or rejecting the unique identifier, automatically overriding the unique identifier and transmit a second unique identifier provided by the user through the user interface to the second apparatus for automatic processing.

15. The method of claim 14, further comprising automatically identifying the at least one of:

one or more surgical instruments used on the anatomical object in the imaging data; or one or more surgical products used on the anatomical object in the imaging data.

16. A surgical system for automatically tracking surgical procedures performed on an anatomical object of a patient, comprising:

a memory comprising executable instructions; and at least one processor configured to execute the executable instructions and cause the surgical system to:

obtain imaging data of the anatomical object of the patient captured during a period of time, the imaging data comprising a plurality of image frames captured during the period of time;

automatically generate a unique identifier corresponding to at least one surgical procedure performed on the anatomical object during the period of time based on the imaging data;

automatically cause a visual representation associated with the at least one surgical procedure and the generated unique identifier to be provided on a user interface;

upon receiving a confirmation from a user confirming the unique identifier, automatically transmit the unique identifier to a second apparatus for automatic processing;

upon receiving user input contradicting or rejecting the unique identifier, automatically override the unique identifier and transmit a second unique identifier provided by the user through the user interface to the second apparatus for automatic processing; and select at least one of a representative image frame or a representative video clip that demonstrates performance of the at least one surgical procedure, wherein the selection is based on a confidence score being greater than or equal to a confidence threshold, the confidence score indicating a level of confidence that the at least one surgical procedure is demonstrated in the selected at least one of a representative image frame or a representative video clip.

17. The surgical system of claim 16, wherein the at least one processor is further configured to cause the surgical system to automatically transmit, to the second apparatus, the at least one of a representative image frame or a representative video clip that demonstrates performance of the at least one surgical procedure.

18. The surgical system of claim 17, wherein:

in order to automatically transmit the unique identifier and the at least one of a representative image frame or a representative video clip to the second apparatus, the at least one processor is further configured to cause the surgical system to generate a patient record; and the patient record includes an indication of the at least one surgical procedure, the unique identifier corresponding to the at least one surgical procedure, and the at least one of a representative image frame or a representative video clip that demonstrates performance of the at least one surgical procedure.

19. The surgical system of claim 18, wherein the at least one processor is further configured to cause the surgical system to include in the patient record a time-stamp indicating when the at least one of a representative image frame or a representative video clip was captured.

20. The surgical system of claim 17, wherein:

the visual representation provided on the user interface further includes the selected at least one of a representative image frame or a representative video clip; and in order to automatically transmit the representative image frame or representative video clip to the second apparatus, the at least one processor is further configured to:

upon receiving a confirmation from a user confirming the unique identifier, automatically transmit the representative image frame or representative video clip to the second apparatus for automatic processing; and upon receiving user input contradicting or rejecting the representative image frame or representative video clip, automatically override the representative image frame or representative video clip and transmit a second representative image frame or representative video clip, provided by the user through the user interface, to the second apparatus for automatic processing.

* * * * *